United States Patent [19]

Cawse

[11] Patent Number: 4,737,569
[45] Date of Patent: Apr. 12, 1988

[54] PROCESS FOR THE PRODUCTION OF SUBSTANTIALLY MONOESTER-FREE DIARYL ESTERS OF AROMATIC DICARBOXYLIC ACIDS

[75] Inventor: James N. Cawse, Pittsfield, Mass.

[73] Assignee: General Electric Company, Pittsfield, Mass.

[21] Appl. No.: 947,686

[22] Filed: Dec. 30, 1986

[51] Int. Cl.$^4$ .............................................. C08G 63/22
[52] U.S. Cl. ...................................... 528/179; 528/180
[58] Field of Search ................................ 528/179, 180

[56] References Cited

U.S. PATENT DOCUMENTS

| | | | |
|---|---|---|---|
| 3,413,336 | 11/1968 | Hulsmann et al. | 260/475 |
| 3,694,490 | 9/1972 | Witt et al. | 260/475 |
| 4,066,623 | 1/1978 | Besso et al. | 528/179 |
| 4,124,566 | 11/1978 | Saiki et al. | 528/177 |
| 4,334,053 | 6/1982 | Freitag et al. | 528/179 |
| 4,430,493 | 2/1984 | Rieder | 528/179 |
| 4,451,664 | 5/1984 | Randae | 560/86 |
| 4,482,732 | 11/1984 | Ranade | 560/86 |
| 4,482,733 | 11/1984 | Ranade | 560/86 |

OTHER PUBLICATIONS

Kurisu et al., *Chemical Abstracts*, 104:33880f.
Fox et al., *Chemical Abstracts*, 96:180991n.
Fox et al., *Chemical Abstracts*, 96:180990m.
Sumitomo Chemical Co., Ltd., *Chemical Abstracts*, 94:65338b.
Toray Industries, Inc., *Chemical Abstracts*, 100:209405p.
Teijin Ltd., *Chemical Abstracts*, 101:6847g.

*Primary Examiner*—Lucille M. Phynes
*Attorney, Agent, or Firm*—Hedman, Gibson, Costigan & Hoare

[57] ABSTRACT

An improved process for the preparation of a diaryl ester containing only small amounts of the corresponding monoesters comprises reacting a mixture of an aryl diacid, a monohydroxy aromatic compound and a catalyst, cooling, adding a controlled amount of water, and cooling further. Typically, diaryl esters, such as diphenyl isophthalate (DPI), containing only about 1–5% of the monoester, such as monophenyl isophthalate are obtained upon addition to the reaction mixture of approximately 5–15% by weight of water at 60°–80° C., followed by cooling to about 15°–35° C.

15 Claims, No Drawings

PROCESS FOR THE PRODUCTION OF SUBSTANTIALLY MONOESTER-FREE DIARYL ESTERS OF AROMATIC DICARBOXYLIC ACIDS

The present invention relates to a novel improved process for preparing diaryl esters of aromatic dicarboxylic acids. More particularly, the invention relates to a simple, low cost method for recovering diaryl esters of aromatic dicarboxylic acids, such as isophthalic and terephthalic, substantially free of the corresponding monoaryl esters. Diaryl esters are useful in the production of linear polyesters, which are important thermoplastic materials due to their excellent performance at high temperatures.

BACKGROUND OF THE INVENTION

Diaryl esters of aromatic dicarboxylic acids have been produced by a number of reactions. Foremost among these is the reaction of aromatic dicarboxylic acids, such as isophthalic and terephthalic acids with an aromatic monohydroxy compound, for example phenol. The basic process has been improved or modified in a number of ways.

By way of illustration, in U.S. Pat. No. 3,413,336 an additional agent, acetic anhydride, is employed in carrying out this reaction which is used with equivalent amounts or a slight excess of a phenol (col. 2, lines 31–32). In col. 3, lines 2–3, it is also taught that it is generally not advisable for reasons of economics, to use excess phenol of more than 25%. The specific examples I-V disclose respectively 2 moles+25%, 2 moles+10%, 2 moles+20% and 2 moles+20%.

In U.S. Pat. No. 4,124,566 it is disclosed that in the most preferred state of the esterification reaction the aromatic monohydroxy compound, e.g., phenol, is present only in a low concentration in the aromatic dicarboxylic acid slurry (col. 6, lines 29–34). In the Examples, the molar ratio of the acid to the phenol is about 1 to 4 and 1 to 6 moles. Furthermore, an aromatic hydrocarbon medium such as ethylbenzene is required in the process.

Neither of the above-mentioned patents, U.S. Pat. No. 3,413,336 or U.S. Pat. No. 4,124,566, refer to or deal with the half ester impurity or its conversion to the diester. In U.S. Pat. No. 3,413,336, col. 3, lines 39–42 it is disclosed that the diaryl esters are obtained in a yield of over 90%. It is taught that they may be easily obtained in any desired degree of purity by simple distillation or recrystallization. In Examples I-IV the diaryl ester is distilled off to give yields of 93%, 90%, and 90.5% respectively.

In U.S. Pat. No. 4,124,566, which is concerned with preparing polyesters, the diaryl ester product obtained in the first step is directly converted into a polymer by reaction with an aromatic dihydroxy compound, such as bisphenol A. There is no mention of a half ester or purification of the diaryl ester product either by crystallization or distillation before it is converted into the polymer.

Witt et al., U.S. Pat. No. 3,694,490 discloses the production of the diphenyl ester of terephthalic and isophthalic acid to the exclusion of the corresponding monophenyl ester, by the continuous removal of water by-product from the reaction zone of a heated solution of reactants. Witt et al. suggest that crystallization of the ester, upon cooling, from a monofunctional phenol provides extremely good purification (col. 4, lines 51–52) but they do not disclose any level of purity for the ester or means for crystallizing other than cooling.

Ranade, U.S. Pat. No. 4,451,664; 4,482,732 and 4,482,733, discloses processes for manufacturing diaryl esters of dicarboxylic acids, such as diphenyl isophthalate (DPI) and diphenyl terephthalate (DPT). In U.S. Pat. No. 4,451,664, the esterification reaction is optimized by continuously removing water and other by-products from the reactor while supplying to the reactor a make-up amount of phenol containing no more than about 100 ppm of water. The make up stream may be obtained by stripping the by-product stream of water and other reaction by-products. In U.S. Pat. No. 4,482,732, water and/or lower alkyl alcohols are distilled from the reaction mixture by varying the reflux ratio during the course of reaction. In U.S. Pat. No. 4,482,733, the esterification reaction is optimized by gradually increasing the temperature during reaction in accordance with the degree of esterification. All of these processes suffer from a drawback in that a significant amount of energy must be expended to obtain a degree of esterification of 95% or higher.

In Japanese Patent Application, No. 60/39067, DPT and DPI are reported to be produced in 100% conversion by adding diaryl esters and aromatic hydrocarbons to the reaction mixture before the esterification reaches 20% completion, followed by refluxing. This process is also deficient in the sense that considerable energy must be expended in the recycling of materials to make the diphenyl ester.

Japanese Patent Application No. 59/36644 describes the purification of DPT by recrystallization from aromatic solvents containing amines with no active hydrogens. It would be more desirable, however, to purify diphenyl esters without using amine components.

In Japanese Patent Application, No. 58/213734, DPT is prepared by transesterification of meta- and para-methylbenzoate with phenyl acetate to give high yield (96%) of DPT. This method is disadvantageous because it uses costly reactants to produce the diphenyl ester, and it is not a simple direct esterification.

Japanese Patent No. 55/100339 describes the preparation of diphenyl esters by reacting a carboxylic acid and a diaryl carbonate at 150–350° C. with stirring to give high yields, e.g., 99.5% of DPT. This transesterification process uses costly reactants to make diphenyl esters and is not preferred for this reason.

In European Patent Applications Nos. 44509 and 44510, Jan. 27, 1982, are disclosed processes for preparation of DPI and DPT. In EP No. 44509, the corresponding acid is reacted with diphenyl carbonate in the presence of catalyst to recover the diphenyl ester. In EP No. 44510, high yields of diesters (90–95%) plus a 5–10% yield of the corresponding monoaryl ester or half ester acid are said to be obtained by reacting the aromatic dicarboxylic acid with large molar excess of phenol and removing the water formed during reaction. Neither of these processes provide for yields of a diaryl ester product that contains less than 1 to 5% of the corresponding intermediate monoaryl ester or half ester acid.

In view of the foregoing, it is unexpected now to discover that diaryl esters of aromatic dicarboxylic acids can be easily produced containing less than 1 to 5% of the corresponding half ester if water is added to the reaction mixture and if the temperature during recovery is carefully controlled. The process of the invention is simple, requires low expenditures of energy, does not involve transesterification, and does not use expensive reactants, such as diaryl carbonate. Phenol or other aryl hydroxy compounds are reactants and water is a by-product in the direct esterification reaction. In distinction to the prior art, also, more water is added herein. This novel method of synthesis also advantageously permits the catalyst and unreacted components to be recycled to the reaction efficiently.

SUMMARY OF THE INVENTION

In accordance with the invention herein is provided an improved process for the preparation of a diaryl ester of an aromatic dicarboxylic acid containing a relatively low proportion of the corresponding monoaryl ester by:
(i) heating from about 200° C. to about 400° C. a mixture comprising
  (a) an aromatic dicarboxylic acid,
  (b) a large molar excess of an aromatic monohydroxy compound, and
  (c) an effective amount of metal catalyst, and
(ii) removing the water formed during the reaction and a major proportion of the unreacted aromatic monohydroxy compound, in which the improvement comprises the steps of thereafter
(iii) cooling the reaction mixture to a temperature in the range of from about 80° C. to 120° C., preferably 80° to 100° C.,
(iv) adding
  (d) water in an amount of from about 5 to about 15 percent, by weight, based on the weight of the reaction mixture; and
(v) further cooling the mixture from step (iv) to a temperature in the range of from about 50° C. to about 80° C., preferably 60° to 90° C., whereby said diaryl ester having a low content of the corresponding monoaryl ester is precipitated.

DETAILED DESCRIPTION OF THE INVENTION

In general the process of the subject invention comprises reacting a mixture comprising the aromatic dicarboxylic acid with a large molar excess of an aromatic monohydroxy compound which reacts with said acid, and in which said acid is soluble, and with which it forms a solution, and a catalyst. The reaction is carried out by heating the mixture at an elevated temperature in the range of from about 200° C. to about 400° C. to form the diaryl ester, and removing water formed during the reaction and a major portion of the unreacted aromatic monohydroxy compound. The aromatic monohydroxy compound serves as a carrier to remove the water, said reaction resulting in a mixture of about 90–95% of the diaryl ester and about 5–10% of the corresponding monoaryl ester of the dicarboxylic acid.

As aromatic dicarboxylic acids it is preferred to use a member of the group consisting of isophthalic and terephthalic acid, and their derivatives such as 5-chloroisophthalic or methylterephthalic or dichloroterephthalic acid.

By aromatic monohydroxy compound is meant compounds having at least one hydroxyl group directly attached to the aromatic ring. As an example of the aromatic monohydroxy compounds it is preferred to use phenol. Other examples are isomeric cresols, or xylenols, butylphenol, benzylphenol, m-cresol, and beta-naphthol, and the like.

In typical reactions, the aromatic monohydroxy compound is employed in a molar ratio of about 1 mole of the aromatic dicarboxylic acid to about 10 to 50, preferably 15 to 20, moles of the aromatic monohydroxy compound.

The heating and distillative removal of by-product water and aromatic hydroxy compound is carried out at an elevated temperature, for example, of about 275° C. to about 300° C. for about 1 hour to about 6 hours, preferably 4 to 6 hours. This generally suffices to remove 90–95% of the water of reaction which translates into a 90–95% yield of the diester.

The esterification reaction is carried out in the presence of a metal catalyst, such as stannous oxide (SnO), in an amount of 0.1 to 0.5 mole percent based on the aromatic dicarboxylic acid. Other catalysts are suitable including stannous acetate, dibutyl tin oxide, antimony oxide, antimony acetate, antimony trioxide, lead oxide and lead acetate. The resulting product typically comprises about 90–95% of the diaryl ester of the aromatic dicarboxylic acid plus a significant content, e.g., about 5–10% of the corresponding monoaryl, or half ester, of the aromatic dicarboxylic acid.

Purification of the aforesaid product in accordance with this invention is carried out by adding an amount of water of from about 5 to about 15%, preferably about 10%, by weight to the mixture after the reaction has been completed and the mixture has been cooled down to a temperature in the range of from about 80° C. to about 120° C., preferably 100° C. Generally, the solution will contain 30 to 50% by weight, preferably 40 to 50%, of diaryl ester, e.g., DPI, with unreacted hydroxy aromatic compound, e.g., phenol, and contaminating amounts of monoaryl ester, e.g., monophenyl isophthalic acid (MPI). Cooling down further the mixture with the added water will crystallize out the desired diaryl ester product, substantially purified of the corresponding monoaryl ester. In general, further cooling the mixture to a temperature in the range of 50° C. to 80° C., with 60° to 70° C. preferably, will suffice. However, in any event, the solution is preferably cooled to about 100° C., water is then added and then the mixture is cooled to about 60° to 70° C. The product precipitates at this point. If desired, equilibrating the crystals at 60° C. to 70° C. is helpful in producing larger, more easily filterable crystals.

Thus, the subject invention provides a process particularly advantageous for the purification of diaryl aromatic esters, e.g., diphenyl isophthalate and diphenyl terephthalate, where these esters are prepared by reacting, e.g., phenol with isophthalic or terephthalic acid, leaving a low content of the corresponding half ester which, in any event, cannot be removed by distillation.

DESCRIPTION OF THE PREFERRED EMBODIMENTS

The following examples illustrate the novel process of the present invention. They are not to be construed to limit the claims in any manner whatsoever.

EXAMPLE 1

Isophthalic acid (1 mole), phenol (15 moles) and stannous oxide (SnO) as catalyst (0.1–0.5) mole % based on the isophthalic acid) are charged into an autoclave, provided with a mechanical stirrer and a needle valve to which is connected a distillation column. The reaction mixture is heated to 300° C. over the course of 1.5 hours during which time the pressure rises to 250 psi. The needle valve is opened and phenol and water formed during the reaction are distilled over the course of three hours. During this period 60% of the original amount of phenol is distilled off. Phenol is used in this reaction, as a reagent, as a solvent for the acid, and as a carrier to remove the water. The initial distilling phenol contains 14% by weight of water while the final distilling phenol contains about 0.2% water.

A product is obtained which contains approximately 50% phenol, 44% of diphenyl ester and 6% of monophenyl ester, as determined by gas-liquid chromatography (GLC). The mixture comprising these products is cooled to a temperature of 100° C. Water, 5% by weight, is added to the mixture which is cooled to 65° C. A precipitate crystallizes out of solution. Analysis indicates DPI is 98.5% pure after removal of phenol, with 1.5% MPI, as determined by GLC.

EXAMPLE 2

The procedure of Example 1 is followed except that terephthalic acid is used in place of isophthalic acid.

The above-mentioned patents, publications, and applications are incoporated herein by reference.

Many variations will suggest themselves to those skilled in the art in light of the above, detailed description. For example, instead of using isophthalic or terephthalic acid, their derivatives, such as 5-chlorisophthalic or methylterephthalic or dichloroterephthalic acid can be used. For example, instead of using stannous oxide, stannous acetate, antimony oxide, antimony acetate, antimony trioxide, lead oxide or lead acetate can be used as metal catalyst. All such variations are within the full intended scope of the appended claims.

I claim:

1. In a process for the preparation of a diaryl ester of an aromatic dicarboxylic acid containing a relatively low proportion of the corresponding monoaryl ester, by:
   (i) heating from about 200° C. to about 400° C. a mixture comprising
   (a) an aromatic dicarboxylic acid,
   (b) a large molar excess of an aromatic monohydroxy compound, and
   (c) an effective amount of a metal catalyst, and
   (ii) removing the water formed during the reaction and a major proportion of the unreacted aromatic monohydroxy compound, in which the improvement comprises the steps of thereafter
   (iii) cooling the reaction mixture to a temperature in the range of from about 80° C. to 120° C.,
   (iv) adding
   (d) water in an amount of from about 5 to about 15 percent, by weight, based on the weight of the reaction mixture; and
   (v) further cooling the mixture from step (iv) to a temperature in the range of from about 50° C. to about 80° C. whereby said diaryl ester having a low content of the corresponding monoaryl ester is precipitated.

2. A process as defined in claim 1 wherein the molar ratio of the aromatic dicarboxylic acid (a) to the aromatic monohydroxy compound (b) is about 1 to from about 15 to about 20.

3. A process as defined in claim 1 in which heating (i) is carried out at from about 250° C. to about 310° C.

4. A process as defined in claim 1 in which heating (i) is carried out at from about 275° C. to about 300° C. from about 4 to about 6 hours.

5. A process as defined in claim 1, wherein the aromatic dicarboxylic acid is a member of the group consisting of isophthalic acid, terephthalic acid, 5-chloroisophthalic acid, methylterephthalic acid and dichloroterephthalic acid.

6. A process as defined in claim 1, wherein the aromatic monohydroxy compound is selected from phenol, isomeric cresols, xylenols, butylphenol, benzylphenol, m-cresol, beta-naphthol.

7. A process as defined in claim 1, wherein the aromatic monohydroxy compound is phenol.

8. A process as defined in claim 1, wherein the aromatic dicarboxylic acid is isophthalic acid.

9. A process as defined in claim 1, wherein the aromatic dicarboxylic acid is terephthalic acid.

10. A process as defined in claim 1, wherein the aromatic dicarboxylic acid is a member of the group consisting of isophthalic acid and terephthalic acid, and the aromatic monohydroxy compound is phenol.

11. A process as defined in claim 1 wherein the diaryl ester is diphenyl isophthalate and the monoaryl ester is monophenyl isophthalate.

12. A process as defined in claim 1 wherein the diaryl ester is diphenyl terephthalate and the monoaryl ester is monophenyl terephthalate.

13. A process as defined in claim 1 wherein the aromatic dicarboxylic acid is a member of the group comprising isophthalic and terephthalic acid, the aromatic hydroxy compound is phenol, the diaryl ester obtained is a member of the group consisting of diphenyl isophthalate and diphenyl terephthalate, and the monoaryl ester is a member of the group consisting of monophenyl isophthalate and monophenyl terephthalate.

14. A process as defined in claim 1 wherein said metal catalyst is selected from stannous acetate, stannous oxide, antimony oxide, antimony acetate, antimony trioxide, lead oxide and lead acetate.

15. A process as defined in claim 1 wherein said catalyst is stannous oxide.

* * * * *